United States Patent [19]

Chen et al.

[11] Patent Number: 5,144,961
[45] Date of Patent: Sep. 8, 1992

[54] ENDOSCOPIC LIGATING DEVICE

[75] Inventors: Chao Chen, Edison; Ralph Spengler, Long Valley, both of N.J.

[73] Assignee: Ethicon, Inc., Somerville, N.J.

[21] Appl. No.: 728,443

[22] Filed: Jul. 11, 1991

[51] Int. Cl.[5] ............................................. A61B 17/00
[52] U.S. Cl. ................................... 128/898; 606/139; 606/148
[58] Field of Search ............... 606/139, 144, 148, 203, 606/1; 128/898

[56] References Cited

U.S. PATENT DOCUMENTS

| | | | |
|---|---|---|---|
| 2,012,776 | 8/1935 | Roeder | 606/139 |
| 3,476,114 | 11/1969 | Shannon et al. | 606/139 |
| 3,476,115 | 11/1969 | Graeff et al. | 606/139 |
| 3,665,926 | 5/1972 | Fiores | 606/139 |
| 4,018,229 | 4/1977 | Komiya | 606/139 |
| 4,244,370 | 1/1981 | Furlow et al. | 606/148 |
| 4,981,149 | 1/1991 | Yoon et al. | 128/898 |

OTHER PUBLICATIONS

Endoknot, Suture Made with Chromic Gut, Ethicon, Inc., 1991.

Primary Examiner—Stephen C. Pellegrino
Assistant Examiner—Gary Jackson

[57] ABSTRACT

Endoscopic ligating device having a surgical needle; a tube; and a filamentary strand attached at its distal end to the surgical needle, and slidably engaged at its proximal end about the tube with a partially tightened knot.

12 Claims, 6 Drawing Sheets

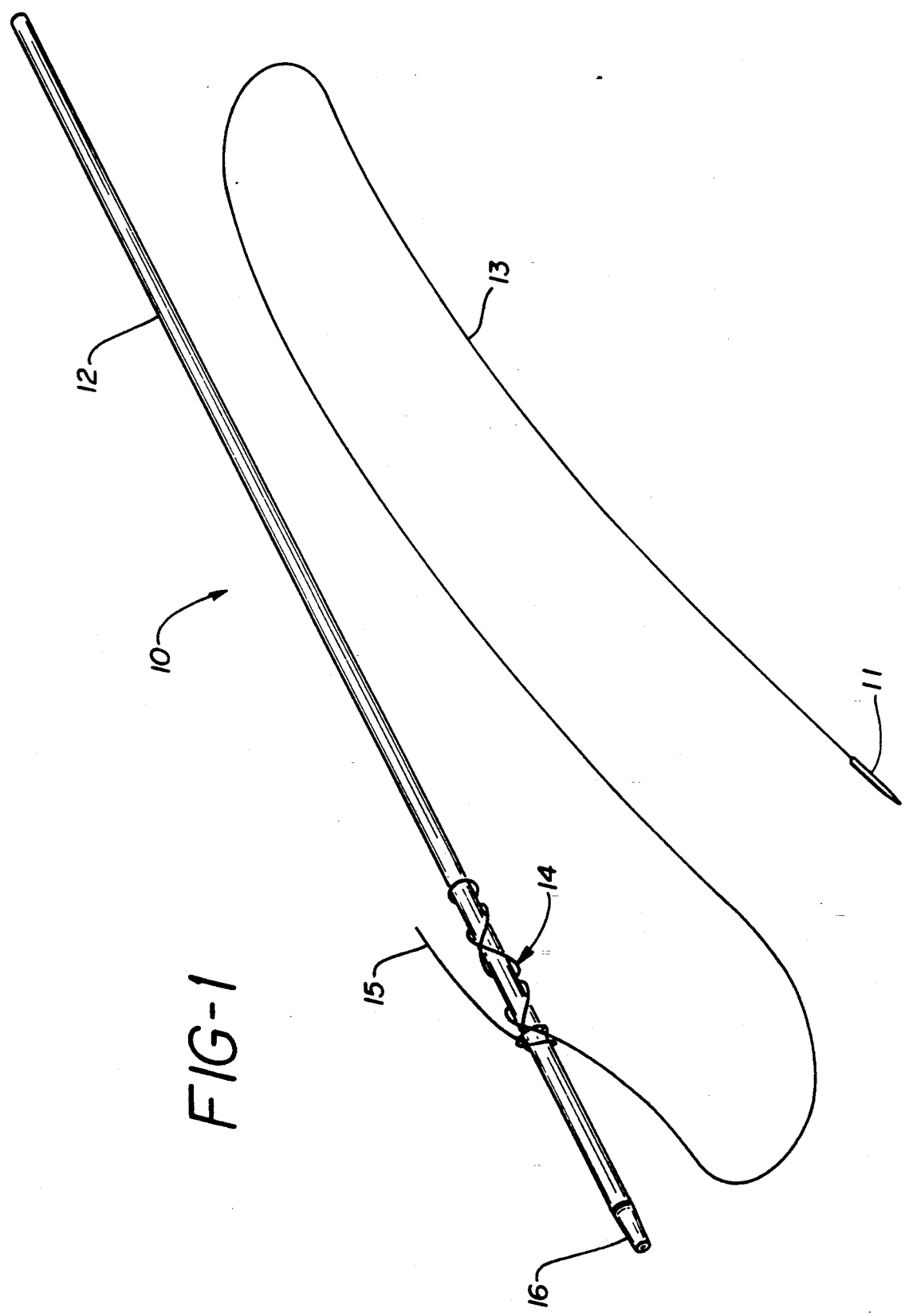

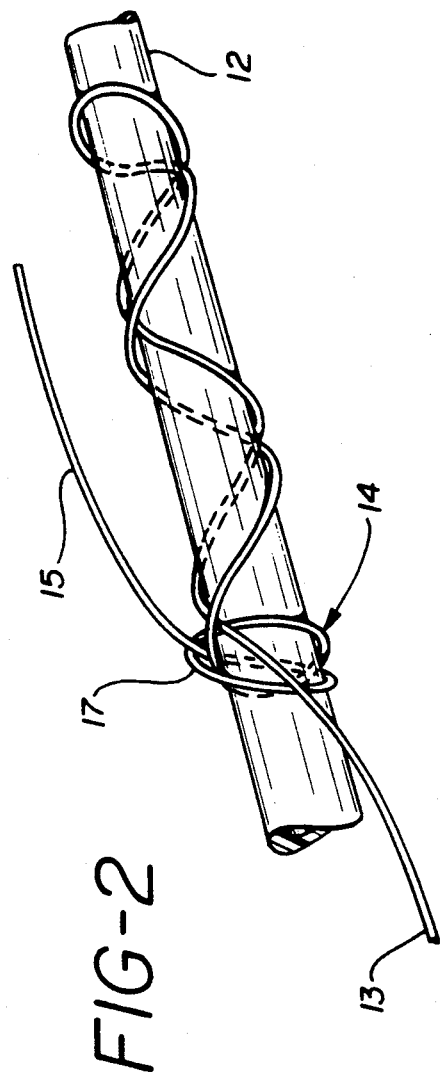
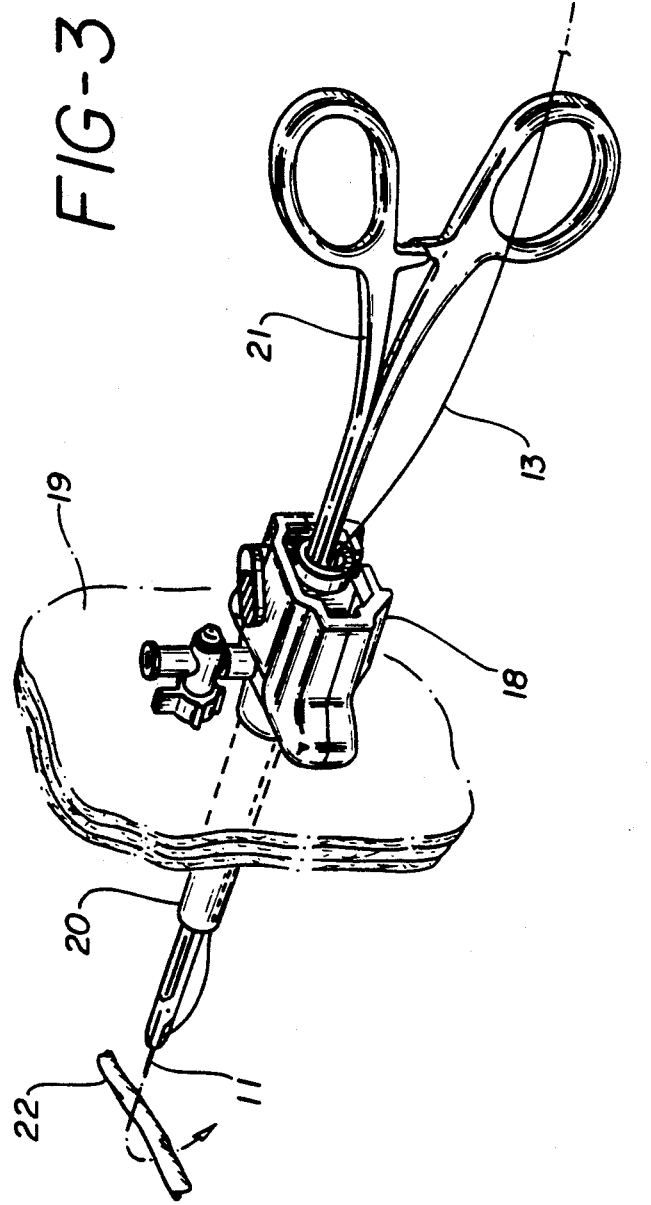

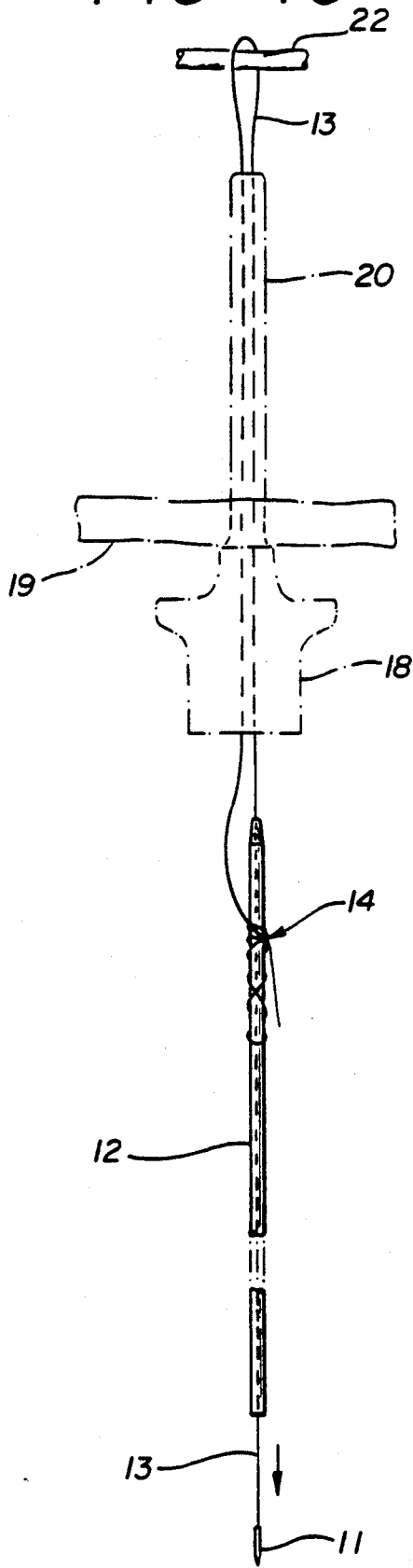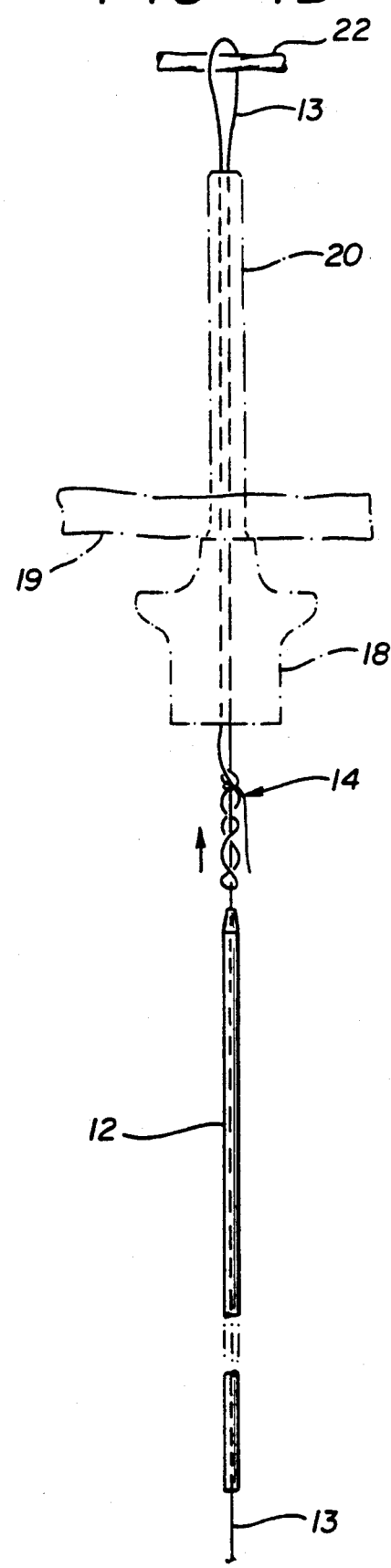

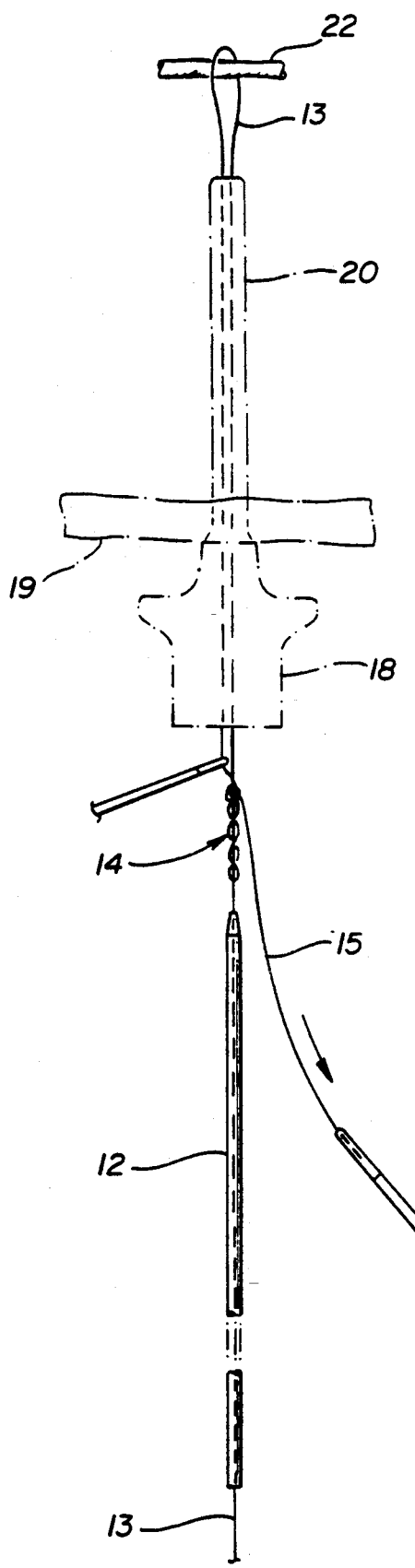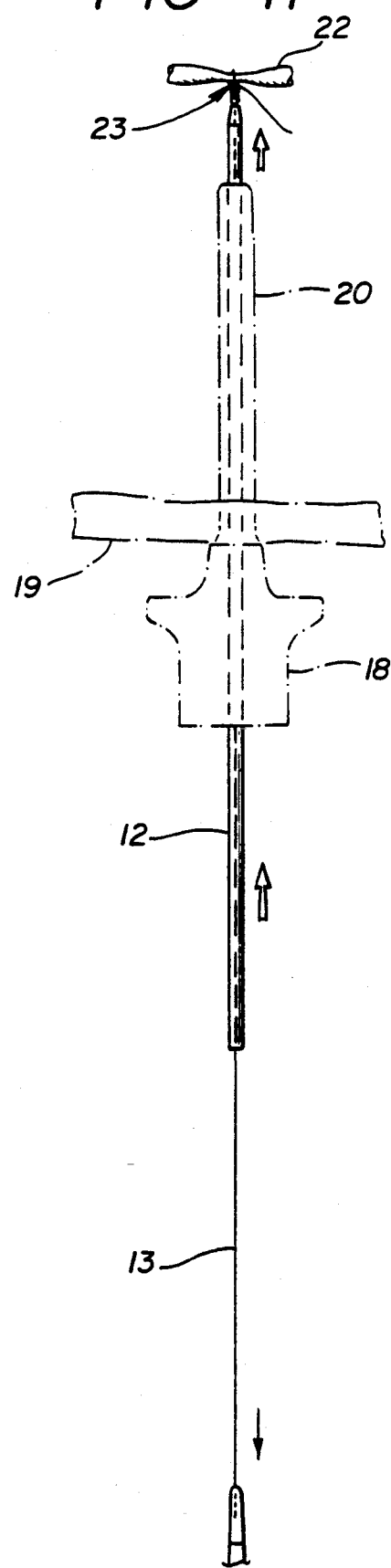

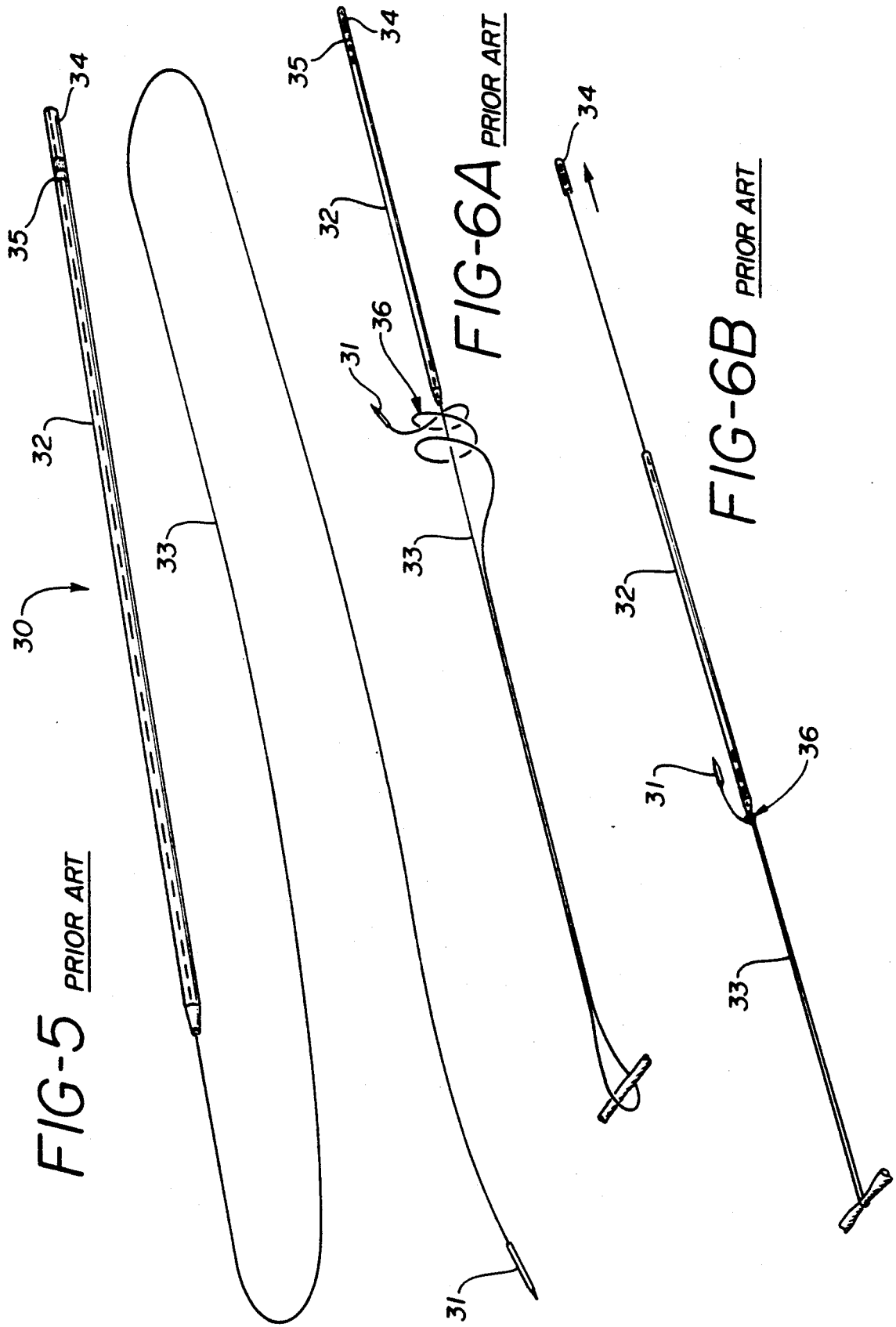

ENDOSCOPIC LIGATING DEVICE

BACKGROUND OF THE INVENTION

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a tube, conventinally referred to as a cannula, after puncture of a hole into the soft tissue protecting the body cavity. The hole is made with a trocar, which is a sharp-pointed instrument. The trocar includes an obturator, or cutting implement, which is slideably and removeably disposed within a trocar cannula. The obturator will puncture a hole in the tissue equal in size to the inner diameter of the trocar cannula. After puncture, the obturator can be slideably withdrawn from the trocar cannula. The surgeon can then perform diagnostic and therapeutic procedures at the surgical site with the aid of specialized instrumentation designed to fit through trocar cannula and additional trocar cannulas providing openings into the desired body cavity as may be required.

In many surgical procedures, including those involving endoscopic surgery, it is often necessary to ligate blood vessels which have been cut within the surgical site. The vessels may then be severed downstream of the ligated portion. The primary reason for ligating the vessels is to maintain the surgical site free of an excess of blood and to reduce blood loss in the patient.

Conventionally, surgeons have closed blood vessels with ligatures, which are long, relatively straight strands of suture material. The surgeon manually ties the ligature around the vessel desired to be closed. Unfortunately, conventional ligatures are not well suited for endoscopic surgical applications where a surgeon's manual operative techniques within the surgical site are severely restricted.

In more recent years, a ligature has been developed which is better adapted for endoscopic surgery. EN-DOKNOT gut ligature is a device formed from a suture material of surgical catgut. The catgut ligature is securely fastened within a cannula at one end and attached to a needle at the other end. As is described and illustrated in more detail herein with respect to the drawings of this prior art device, although ENDOK-NOT gut ligature facilitates ligation of vessels through small incisions in bodily cavities, the surgeon is required to manually tie the ligature knot extracorporeally, i.e. outside the body, to ligate a vessel. This is a time consuming and laborious process, especially for inexperienced surgeons, and represents a significant disadvantage to the use of the ENDOKNOT ligature device.

In view of the significant deficiency of the prior art, an endoscopic ligature which avoids the necessity of manual knot-tying extracorporeally would be highly desired within the medical community.

SUMMARY OF THE INVENTION

The invention is an endoscopic ligating device. The device comprises a surgical needle; a tube; and a filamentary strand attached at its distal end to the surgical needle, and slidably engaged at its proximal end about the tube with a partially tightened knot.

The endoscopic ligating device of this invention is particularly well suited for ligating vessels endoscopically. Significantly, the user of the device is not required to manually tie a knot extracorporeally to ligate the desired vessel.

The device may be used during endoscopic surgery for numerous applications in which the ligation of a bodily vessel is desired.

BRIEF DESCRIPTION OF THE DRAWINGS

FIG. 1 is a perspective view of the endoscopic ligating device of this invention.

FIG. 2 is an enlarged fragmentary perspective view of a portion of the endoscopic ligating device of FIG. 1.

FIG. 3 is a perspective view of conventional surgical instrumentation used in conjunction with the first step in ligating a vessel with the endoscopic ligating device of this invention.

FIGS. 4A through 4F are schematic top plan views illustrating the sequence of steps required to ligate a vessel using the endoscopic ligating device of the invention.

FIG. 5 is a perspective view of a prior art endoscopic ligating device.

FIGS. 6A and 6B are perspective views of the prior art device of FIG. 5 showing in simplified form the steps required to ligate a vessel.

DETAILED DESCRIPTION OF THE PREFERRED EMBODIMENT

Figure 4A:
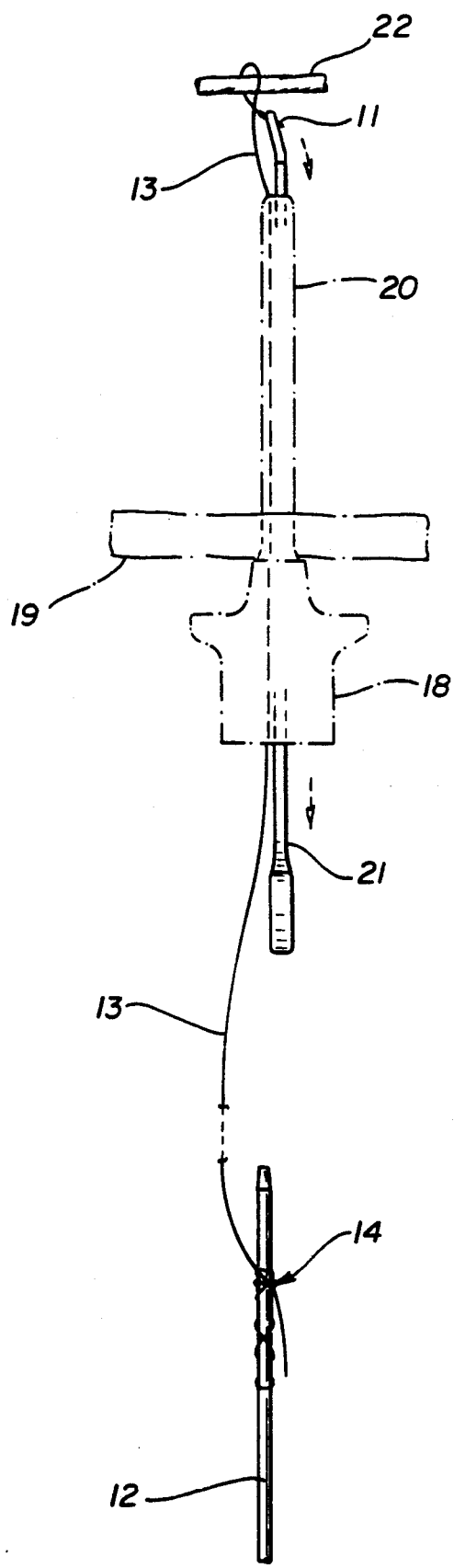

As used in this specification, the word distal is used to describe that portion of the device which extends away from the user during use, and the word proximal is used to describe that portion of the device that extends toward the user during use.

Referring now to FIG. 1, there is shown an endoscopic ligating device 10 within the scope of the present invention. The device has a surgical needle 11, a tube 12, and a filamentary strand 13. The filamentary strand is attached at its distal end to the surgical needle, and is slidably engaged at its proximal end about the tube with a partially tightened knot 14 having a knot pulling end 15. Tube 12 has a tapered distal portion 16, and is shaped as an elongate cylinder with a continuous opening extending axially therethrough. The cross-sectional diameter of the continuous opening at all points along the length of the cylinder is greater than the cross-sectional diameter of the surgical needle and the filamentary strand to facilitate the passage of the needle and the strand through the tube. Tube 12 is preferably composed of a flexible plastic, and the opening extending axially therethrough has a substantially constant cross-sectional diameter.

The filamentary strand 13 can be attached to the needle using standard needle attachment. Alternatively, it can be attached using removable or detachable needle attachment. In the case of standard needle attachment, the strand is securely attached to the needle and is not intended to be separated from the needle except by cutting or severing the strand. Removable needle attachment, by contrast, is such that the needle is separable from the strand in response to a force exerted by the surgeon, as illustrated, for example, in European Patent Application 0 420 605 and U.S. Pat. No. 3,926,194.

The filamentary strand can be composed of any surgical suture material. Suture materials can be composed of synthetic and nonsynthetic filaments, as well as absorbable and nonabsorbable fibers. Examples of suitable nonabsorbable suture materials include, but are not limited to, nylon, polypropylene, steel, and polyethyleneteraphthalate (PET). The preferred suture materials are synthetic bioabsorbable suture materials. Examples of suitable bioabsorbable suture materials are those which are derived from the polymerization of lactone monomers, e.g. glycolide, lactide, p-dioxanone and $\epsilon$-caprolactone.

FIG. 2 illustrates in further detail the knot configuration of the partially tightened knot 14. Specifically, filamentary strand 13 is encircled about the proximal end of the tube to form five loosely engaged loops of the partially tightened knot. The remaining length of the filamentary strand is then extended through a loop formation 17 to form the pulling end 15 of the filamentary strand. It should be understood that the number of loops used in forming the knot 14 is not limited to the specific embodiment shown. All that is necessary is that a partially tighted knot is configured in such a manner that when fully tightened it allows sliding movement in one direction and prevents such sliding movement in the opposite direction.

In operation, the user of the device would pass the surgical needle 11 and a portion of filamentary strand 13 through a trocar into a body cavity where the desired ligation is to occur. As illustrated in FIG. 3, the needle and a portion of the filamentary strand are passed down trocar 18 through bodily tissue 19 and trocar cannula 20 to reach the body cavity. Once the needle has passed through trocar cannula 20, a suitable needle grasping instrument 21 is used to grasp surgical needle 11. The needle is looped around desired vessel 22 by passing the needle in the direction of the arrow as shown.

Figure 4B:
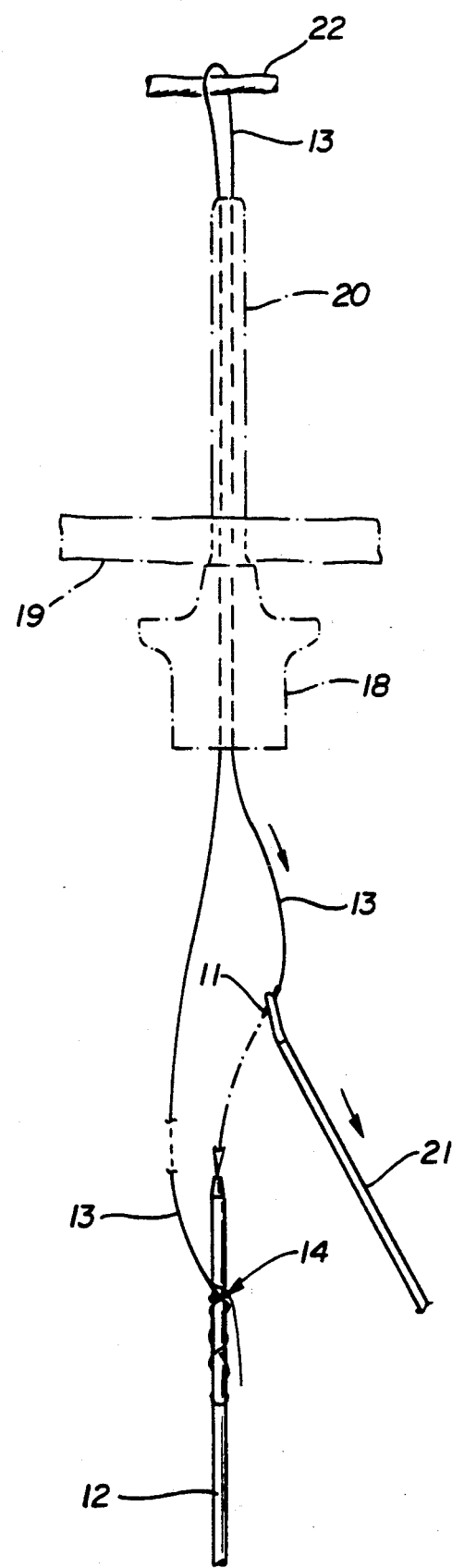

Referring now to FIGS. 4A to F, once the needle is passed around the vessel to be ligated, it is then passed back up through the trocar until the needle and a portion of the strand exit the trocar outside the body. At this point, the needle is removed from the strand. As shown in FIG. 4B, the strand is then inserted into the distal end of tube 14 and passed through the tube proximally until a portion of the strand protrudes from the proximal end of the tube as shown in FIG. 4C. Once the user has a firm grip of the portion of the strand protruding from the proximal end of the tube, the user can then slide partially tightened knot 14 distally on the tube until the partially tightened knot disengages from the tube and is engaged about the filamentary strand, as shown in FIG. 4D. As illustrated in FIG. 4E, the user of the device, while maintaining a firm grip on the portion of the filamentary strand protruding from the proximal end of the tube, can pull the pulling end 15 of the strand in the direction of the arrow as shown to fully tighten the knot. Once the knot is fully tightened, the user can then readily slide the knot distally on the filamentary strand by pushing the knot down with the tapered distal portion of the tube until it firmly engages and ligates vessel 22 as shown if FIG. 4F. After the ligation is completed, the user can then remove the tube from the trocar and sever the filamentary strand at a location near the ligated vessel 22.

To illustrate how this represents a significant advance in the state of the art, FIGS. 5 and 6 illustrate the prior art endoscopic ligating device and its use. There is shown the prior art ligating device 30, which has a needle 31, a tube 32 and a filamentary strand 33. The filamentary strand is housed within tube 32 and is securely fastened at its proximal end to frangible portion 34 of the tube as indicated at score line 35. The distal end of the filamentary strand is attached to the needle. In operation, the user would pass the needle and filamentary strand into the body cavity and loop the needle and strand about the vessel to be ligated. The needle and strand are then passed outside the body where the user must then manually tie an appropriate knot formation 36. Once knot formation 36 is accomplished, the user then breaks frangible portion 34 of tube 32 about score line 35, and then pulls the frangible portion proximally in the direction of the arrow as shown. This movement, in conjunction with the movement of the knot formation 36 distally on the filamentary strand will engage and firmly ligate the desired bodily vessel.

Although this detailed description has focused on the preferred embodiment of the invention, it is readily apparent that numerous additional embodiments can be readily achieved without departing from the spirit and scope of the invention.

What is claimed is:

1. A method of ligating a vessel endoscopically, comprising the steps of:
   a) providing an endoscopic ligating device, said device having a surgical needle, a tube, and a filamentary strand attached at its distal end to the surgical needle, and slideably engaged at its proximal end about said tube with a partially tightened knot;
   b) passing said surgical needle down through a trocar into a body cavity wherein the desired ligation is to occur;
   c) looping said needle around said vessel;
   d) passing said surgical needle up through said trocar until said needle exits said trocar;
   e) removing said needle from said filimentary strand;
   f) inserting said strand into the distal end of said tube and passing said strand up through said tube until a portion of said strand protrudes from the proximal end of said tube;
   g) sliding said partially tightened knot distally on the tube until said partially tightened knot disengages from said tube and is engaged about said filamentary strand;
   h) tightening said partially tightened knot about said strand so as to form a fully tightened knot; and
   i) sliding said fully tightened knot distally on said strand until said fully tightened knot firmly engages and ligates said vessel.

2. The method of claim 1 wherein the tube is an elongate cylinder having a continuous opening extending axially therethrough.

3. The method of claim 2 wherein the cross-sectional diameter of the continuous opening is greater than the cross-sectional diameter of the surgical needle and the filamentary strand so as to allow passage of the needle and the strand through the tube.

4. The method of claim 3 wherein the partially tightened knot is engaged about the tube with five loops disposed around the circumference of the tube.

5. The method of claim 4 wherein the partially tightened knot terminates with a pulling end of the filamentary strand, wherein the knot can be fully tightened by pulling said pulling end.

6. The method of claim 5 wherein the knot, when fully tightened, is configured to allow sliding movement in one direction and to prevent sliding movement in the opposite direction.

7. The method of claim 6 wherein the fully tightened knot is adapted to ligate a bodily vessel.

8. The method of claim 7 wherein continuous opening of the the elongate cylinder has a substantially constant cross-sectional diameter.

9. The method of claim 8 wherein the elongate cylinder has a tapered distal portion.

10. The method of claim 9 wherein the elongate cylinder is composed of a flexible plastic.

11. The method of claim 10 wherein the filamentary strand is composed of a surgical suture material.

12. The method of claim 11 wherein the suture material is bioabsorbable.

* * * * *